(12) United States Patent
Han et al.

(10) Patent No.: US 7,592,367 B2
(45) Date of Patent: Sep. 22, 2009

(54) **COMPOUNDS FROM *GARCINIA HANBURYI*, THEIR USE IN TREATING CANCER AND METHOD OF SEPARATING EPIMERS THEREOF**

(75) Inventors: Quan-Bin Han, Hong Kong (HK); Jing-Zheng Song, Hong Kong (HK); Chun-Feng Qiao, Hong Kong (HK); Ling Yang, Dalian (HK); Hong-Xi Xu, Hong Kong (HK)

(73) Assignee: Hong Kong Jockey Club Institute of Chinese Medicine Ltd., Shatin, Hong Kong (CN)

( * ) Notice: Subject to any disclaimer, the term of this patent is extended or adjusted under 35 U.S.C. 154(b) by 47 days.

(21) Appl. No.: 11/614,089

(22) Filed: Dec. 21, 2006

(65) Prior Publication Data

US 2007/0149610 A1 Jun. 28, 2007

Related U.S. Application Data

(60) Provisional application No. 60/752,961, filed on Dec. 23, 2005.

(51) Int. Cl.
*A61K 31/352* (2006.01)
*C07D 311/78* (2006.01)

(52) U.S. Cl. ........................ 514/453; 549/381

(58) Field of Classification Search ................. 514/453; 549/381
See application file for complete search history.

(56) References Cited

OTHER PUBLICATIONS

Miller et al, J. Chromatography A, vol. 865 (1999) pp. 211-226.*
Guo et al., "General gambogic acids inhibited growth of human hepatoma SMMC-7721 cells in vitro and in nude mice," Acta Pharmacol Sin, 25(6), pp. 769-774, 2004.
Zhang et al., "Discovery, characterization and SAR of gambogic acid as a potent apoptosis inducer by a HTS assay," Bioorganic & Medicinal Chemistry, 12, pp. 309-317, 2004.
Zhao et al., "Gambogic Acid Induces Apoptosis and Regulates Expressions of Bax and Bcl-2 Protein in Human Gastric Carcinoma MGC-803 Cells," Biol. Pharm. Bull., 27(7), pp. 998-1003, 2004.
Wu et al., "Gambogic Acid Inhibits Proliferation of Human Lung Carcinoma SPC-A1 Cells in Vivo and in Vitro and Represses Telomerase Activity and Telomerase Reverse Transcriptase mRNA Expression in the Cells," Biol. Pharm. Bull., 27(11), pp. 1769-1774, 2004.
Guo et al., "Gambogic Acid Inducing Apoptosis in Human Gastric Adenocarcinom SGC-7901 Cells," Chin J Nat Med, vol. 2, No. 2, pp. 106-110, 2004.
Weakley et al., "Crystal structure of the pyridine salt of gambogic acid," Journal of Chemical Crystallography, 31 (11-12), 501-505, 2001, 41 pages.
Lei et al., "Retrospect and Prospect of Anti-cancer Efficacy of Gamboge," China J Cancer Prev Treat, vol. 10, No. 2, pp. 216-219, 2003, only Abstract in English.
Lin et al., "Isogambogic acid and Isomorellinol from *Garcinia hanburyi*," Magnetic Resonance in Chemistry, vol. 31, pp. 340-347, 1993.
Asano et al., "Cytotoxic Xanthones from *Garcinia hanburyi*," Phytochemistry, vol. 41, No. 3, pp. 815-820, 1996.
Prasad et al., "Antidermatophytic activity of extracts from *Psoralea corylifolia* (Fabaceae) correlated with the presence of a flavonoid compound," Journal of Ethnopharmacology, 91, pp. 21-24, 2004.
Khatune et al., "Antibacterial compounds from the seeds of *Psoralea corylifolia*," Fitoterapia, 75, pp. 228-230, 2004.
Takizawa et al., "Sequential analysis of testicular lesions and serum hormone levels in rats treated with a *Psoralea corylifolia* extract," Food and Chemical Toxicology, 42, pp. 1-7, 2004.
Whelan et al., "Ethanolic extracts of *Euphorbia* and other ethnobotanical species as inhibitors of human tumour cell growth," Phytomedicine, 10, pp. 53-58, 2003.
Beringer et al., "Transporters and their impact on drug disposition," Ann Pharmacother, 39, pp. 1097-1108, 2005.
Antoniou et al., "Interactions between antiretrovirals and antineoplastic drug therapy," Clin Pharmacokinet, 44, pp. 111-145, 2005.
Mosmann, "Rapid colorimetric assay for cellular growth and survival: application to proliferation and cytotoxicity assay," J Immunol Method, 65, pp. 55-63, 1983.
Sanderink et al., "Involvement of human CYP1A isoenzymes in the metabolism and drug interactions of riluzole in vitro," J Pharm Exper Therap, 282, pp. 1465-1472, 1997.

* cited by examiner

*Primary Examiner*—Taofiq A Solola
(74) *Attorney, Agent, or Firm*—George G. Wang; Wilkinson & Grist

(57) ABSTRACT

Three pairs of C-2 epimeric xanthones isolated from *Garcinia hanburyi* and method for efficiently separating the xanthone compounds into individual epimers, each of which possesses varying biological effects. The compounds are useful for their anticancer effects, particularly because they are shown to be non-substrates of the multidrug-resistance transporter. Some of the epimers have significant inhibitory effects on cytochrome P450 systems. The xanthone compounds of the present invention are gambogic acid, epigambogic acid, isogambogic acid, isoepigambogic acid, 30-hydroxygambogic acid and 30-hydroxyepigambogic acid.

4 Claims, 3 Drawing Sheets

COMPOUNDS FROM *GARCINIA HANBURYI*, THEIR USE IN TREATING CANCER AND METHOD OF SEPARATING EPIMERS THEREOF

CROSS REFERENCE TO RELATED APPLICATIONS

This application claims priority to U.S. Provisional Application No. 60/752,961, filed Dec. 23, 2005, the contents of which are hereby incorporated by reference.

FIELD OF THE INVENTION

This invention relates to novel compounds isolated and purified from the herb medicine *Garcinia hanburi* and their medical applications, and it further relates to a method of separating epimers of the compounds.

BACKGROUND OF THE INVENTION

Gamboges, the resin from various *Garcinia* species including *G. morella* and *G. hanburyi*, is rich in anti-tumor gambogic acid (GA, CAS No. 2752-65-0) [1-7]. Gambogic acid was always isolated as an inseparable C(2) epimeric mixture whose structure could not be determined completely until the (R)-epimer was obtained by recrystallization of the pyridine salt of GA and identified by single crystal X-ray diffraction [8], [9]. As different epimers of the same compounds can have significantly different biological effects and different interactions with other therapeutic agents when used in combination, a common practice in chemotherapy, it is of great importance to be able to separate the epimers of the compounds naturally occuring in the herb gamboges that have anti-tumor effects.

Additionally, MDR in cancer cells is a significant factor for the failure of chemotherapy in many patients. It is very important to find and develop new anticancer drug that can overcome MDR of cancer cells, because MDR transporters contributed significantly to the pharmacokinetic disposition of anticancer drugs. Knowledge of substrates, inducers and inhibitors of these transporters is necessary to ensure optimal clinical outcomes [10]. In addition, chemotherapy often requires multidrug combination, and most anti-cancer drugs are metabolic substrates of cytochrome P450s. Therefore, understanding of drug-drug interactions is important for the combination use of anti-cancer drugs. The likelihood of drug interactions with combination therapy will be very high, if these combined drugs are substrates and potent inhibitors or inducers of the cytochrome P450 (CYP) system [11].

SUMMARY OF THE INVENTION

Accordingly, as an object of the present invention, there is provided a number of novel chemical compounds which are isolated in a pure state for the first time from the herb gamboges. The compounds of the present invention are useful for their anti-tumor effects, particularly when they come with a good understating of their potential interactions with other anti-cancer drugs in terms of their being non substrates of multi-drug resistance (MDR) transporter and their inhibitory effects on various human cytochrome P450 (CYP) systems.

As another object of the present invention, there is provided a method for efficiently separating epimers of xanthone compounds of the herb gamboges. This method greatly facilitates the studies of the active ingredients of gamboges in the effort to provide a better understanding of these compounds' therapeutic applications.

In a particular embodiment, the present invention provides three pairs of C-2 epimeric xanthones from *Garcinia hanburyi*, which are useful for their anticancer effects. The structures of the compounds are shown as follows:

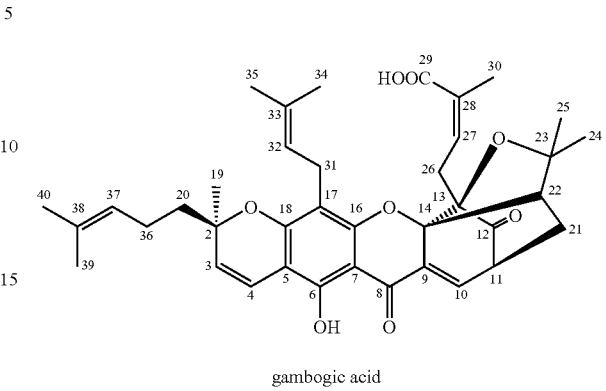

gambogic acid

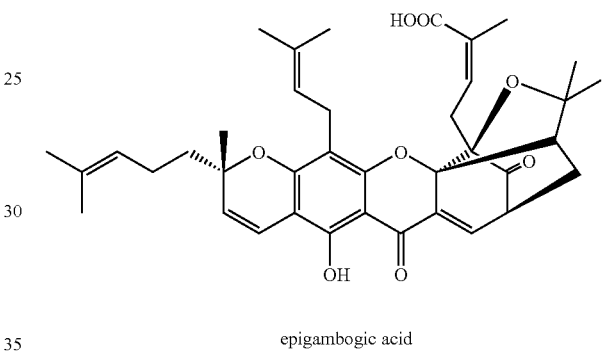

epigambogic acid

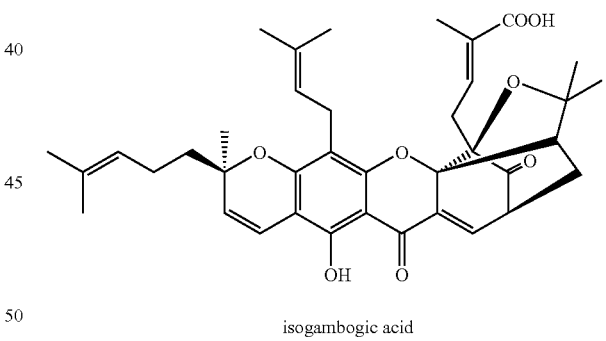

isogambogic acid

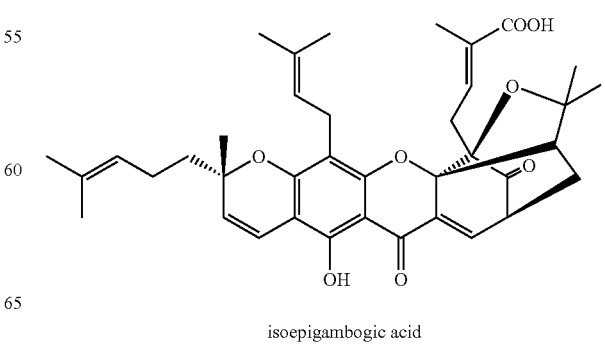

isoepigambogic acid

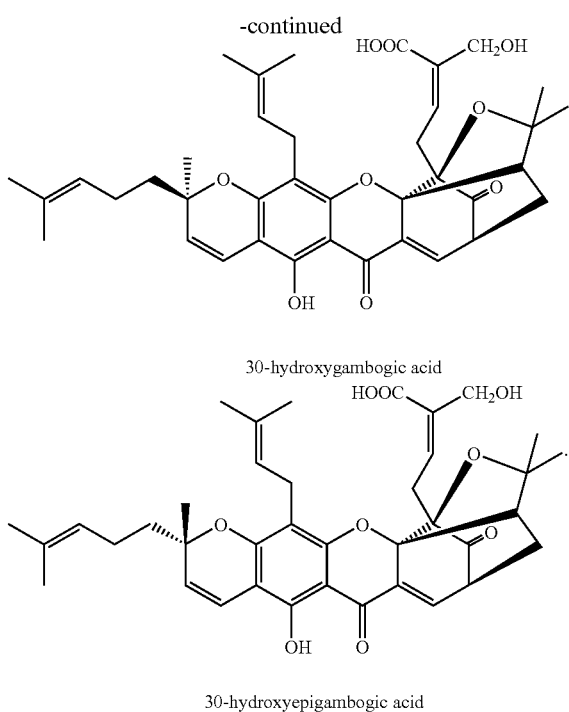

30-hydroxygambogic acid 30-hydroxyepigambogic acid

Gambogic acid (GA, CAS No. 2752-65-0) which was previously isolated as an inseparable stereomeric mixture of C-2 epimers, were separated into two epimers (gambogic acid and epigambogic acid, referred to as 1 and 2) according to the present invention. In the HPLC analysis, GA presented as one peak (m/z 628) on $C_{18}$ column (Alltima $C_{18}$, 5μ, 4.6×250 mm) eluted with CH3CN/0.1% acetic acid (90:10). When the fraction corresponding to the single peak was then subject to $C_8$ column (Alltima $C_8$, 5μ, 4.6×250 mm), eluted with CH3CN/0.1% acetic acid (75:25), two completely separated peaks appear. These two peaks were isolated by HPLC under the same analytical condition with each injection of 20 μL acetone solution of gambogic acid (35 mg/mL), yielding 1 (12 mg) and 2 (10 mg). The two peaks being two C-2 epimers of GA was clearly confirmed by extensive spectroscopic analysis and direct comparison of NMR and HPLC data with those of the known R-epimer. In addition, two similar pairs of C-2 epimeric xanthones were also isolated from this plant by the same method. They were identified to be isogambogic acid, epiisogambogic acid, 30-hydroxygambogic acid, and 30-hydroxyepigambogic acid by extensive spectroscopic and chromatographic analysis including HRMS, 2D NMR, and HPLC techniques. All of these epimers except gambogic acid (R-epimer which had been reported by American scientists using single crystal X-ray diffraction) were isolated and separated for the first time, and 30-hydroxygambogic acid and 30-hydroxyepigambogic acid were previously unknown compounds.

In another aspect of the present invention, both C-2 epimers (Epimers 1 and 2) of gambogic acid were examined for their cytotoxicities against human leukemia K562(K562/S) and doxorubicin-resistant K562 (K562/R) cell lines. Different from doxorubicin (IC50=10.78 for K562/R and 0.66 μM for K562/S), epimers 1 and 2 exhibited similar activities against both cell lines (IC50=1.32 and 0.89 μM for 1, IC50=1.11 and 0.86 μM for 2). These results indicated that both epimers were not multidrug resistance (MDR) substrates. Furthermore, epimers 1 and 2 (R-epimer and S-epimer, respectively) were tested for their inhibitory effects against six human cytochrome P-450 enzymes. Epimers 1 and 2 showed little inhibitory effects toward five of the enzymes except CYP2C9. Furthermore, when tested against CYP2C9, S-epimer had inhibitory effect 20 folds stronger than R-epimer.

DETAILED DESCRIPTION OF THE INVENTION

Example 1

Figure 1:
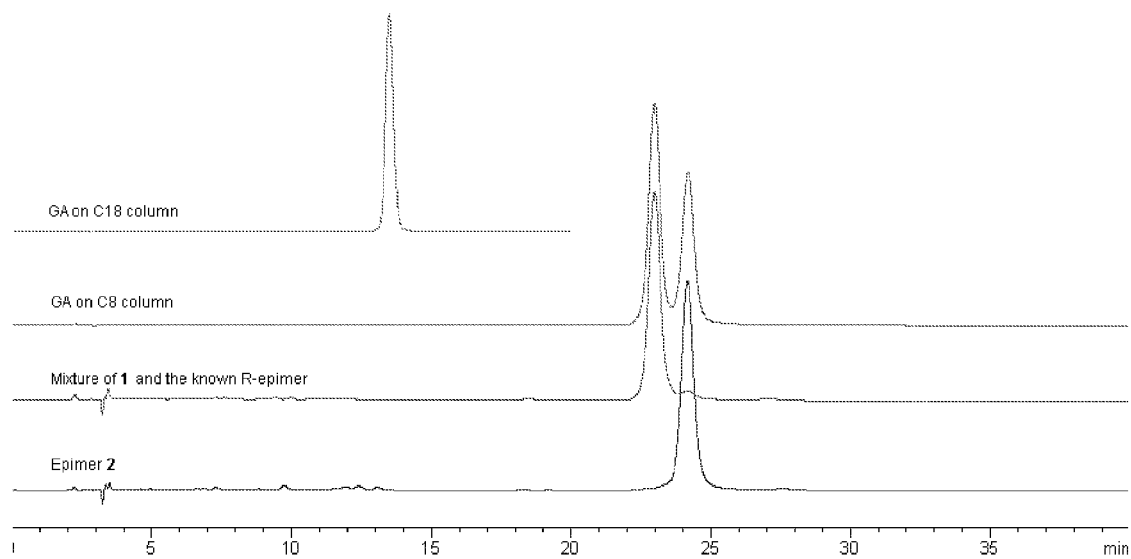
FIG. 1 shows HPLC chromatograms of gambogic acid, the mixture of compound 1, the known R-epimer, and compound 2. Compounds 1 and 2 were identified as R- and S-epimers of gambogic acid in the present invention.
Figure 2:
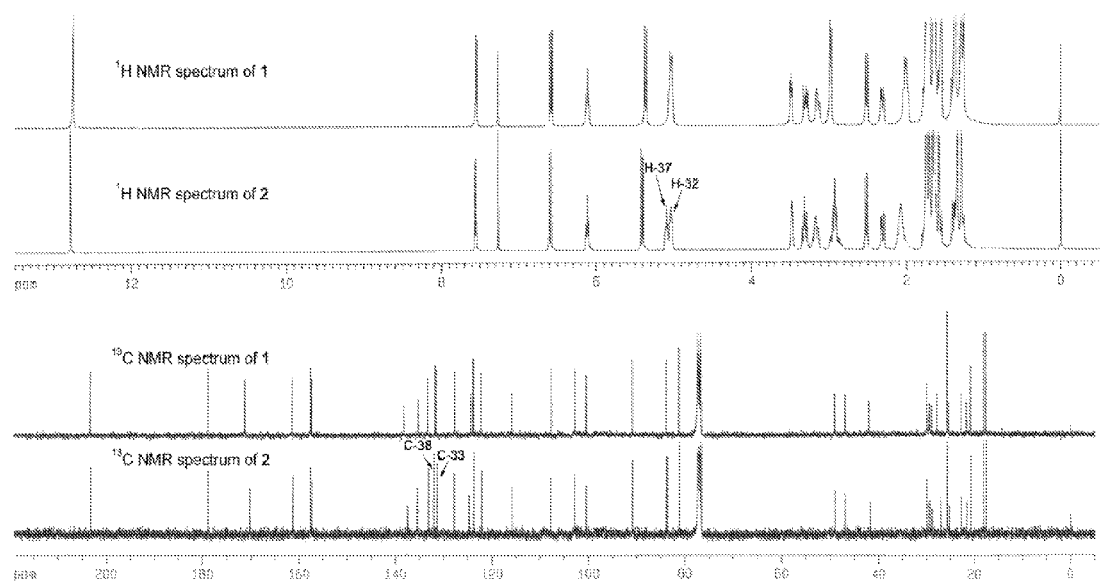
FIG. 2 shows $^1H$ (400 MHz) and $^{13}C$ (100 MHz) NMR spectra of compound 1 and compound 2 (in $CDCl_3$, TMS as internal standard).
Figure 3:
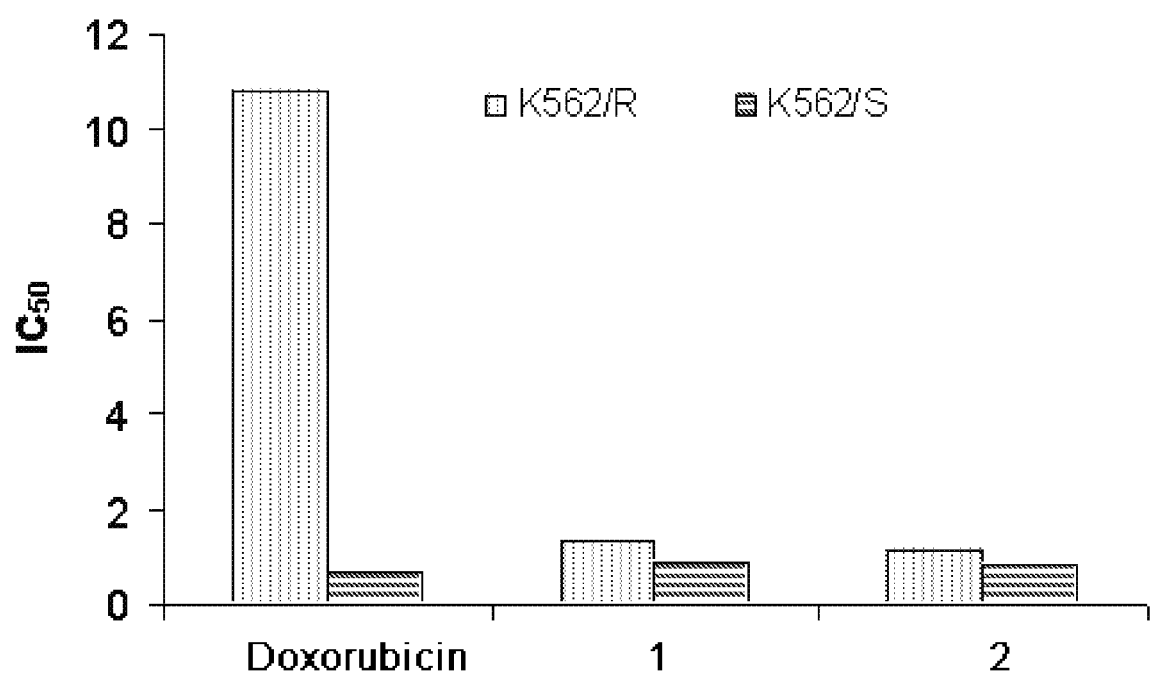
FIG. 3 shows a comparison among the cytotoxic activities of doxorubicin, compound 1, and compound 2 (μM).

R- and S-Epimers of Gambogic Acid (A) Isolation and Identification

The resin (0.1 g) of *Garcinia hanburyi* was purchased from National Institute for the Control of Pharmaceutical and Biological Products (NICPBP), P. R. China. A voucher specimen (CMS-0283) is deposited in the Herbarium of Hong Kong Jockey Club Institute of Chinese Medicine, Hong Kong, China.

The resin (90 mg) was dissolved in 2 mL acetone, and loaded on the preparative HPLC system (Agilent 1100, Alltima $C_{18}$, 10μ, 22×250 mm) to give GA. The mobile phase was MeOH/0.1% $H_3PO_4$ (90:10). The flow rate was 1 mL/min. UV detection wavelength was set at UV 360 nm. After the isolation of GA with prep-HPLC, the GA fraction was condensed to remove most of $CH_3CN$, and the condensed acidified solution was diluted with a large amount of water and loaded on a Sephadex LH-20 CC to remove the acid by eluting with $H_2O$. The subsequent $Me_2CO$ elution was condensed to dry, and GA was obtained (35 mg). In the HPLC/ESIMS analysis, GA presented as one peak (m/z 628) on $C_{18}$ column (Alltima $C_{18}$, 5μ, 4.6×250 mm) eluted with $CH_3CN$/0.1% acetic acid (90:10). However, it presented as two completely separated peaks on $C_8$ column (Alltima $C_8$, 5μ, 4.6×250 mm) eluted with $CH_3CN$/0.1% acetic acid (75:25). These two peaks were isolated by HPLC under the same analytical condition with each injection of 20 μL acetone solution of GA (35 mg/mL), yielding 1 (12 mg) and 2 (10 mg). Gambogic acid (1): a bright yellow amorphous powder. $[\alpha]_D^{20}=-578°$ (c=0.201, $CHCl_3$). UV (MeOH): $\lambda_{max}$=290 (log ε4.24), 360 (log ε4.18). IR (KBr): $\lambda_{max}$=2970, 2928, 1736, 1690, 1632, 1593, 1435, 1331, 1177, 1138, 1049, 810, 671. ESIMS: m/z=628 ($M^+$); HRESIMS: m/z=obsd. 628.3046 $[M]^+$, calcd. 628.3036. Epigambogic acid (2): a bright yellow amorphous powder. $[\alpha]_D^{20}=-486°$ (c=0.197, $CHCl_3$). UV (MeOH): $\lambda_{max}$=290 (log ε4.24), 360 (log ε4.18). IR (KBr): $\lambda_{max}$=2971, 2930, 1736, 1691, 1633, 1593, 1435, 1332, 1177, 1138, 1048, 810, 671. ESIMS: m/z=628 ($M^+$); HRESIMS: m/z=obsd. 628.3042 $[M]^+$, calcd. 628.3036. Copies of the original spectra are obtainable from the author of correspondence.

Optical rotations were measured with a Jasco P-1010 Polarimeter. 1H-(400 MHz) and 13C-(100 MHz) NMR spectra were recorded on Brucker DRX-400 spectrometer using TMS as an internal standard. The LC/MS analysis was performed using an Agilent 1100 series combined with MICROMASS Q-TOF-2 spectrometer.

TABLE 1

$^1$H and $^{13}$C NMR data of 1 and 2$^a$.

| No. | 1 $^1$H | 1 $^{13}$C | 2 $^1$H | 2 $^{13}$C |
|---|---|---|---|---|
| 2 | | 81.27 s | | 81.13 s |
| 3 | 5.35, d, 10.0 | 124.46 d | 5.39, d, 10.0 | 124.81 d |
| 4 | 6.57, d, 10.0 | 115.88 d | 6.57, d, 10.0 | 115.91 d |
| 5 | | 102.72 s | | 102.91 s |
| 6 | | 157.55 s | | 157.61 s |
| 6-OH | 12.73 s | | 12.76 s | |
| 7 | | 100.43 s | | 100.51 s |
| 8 | | 178.86 s | | 178.92 s |
| 9 | | 133.36 s | | 133.24 s |
| 10 | 7.53, d, 6.8 | 135.30 d | 7.53, d, 6.8 | 135.50 d |
| 11 | 3.46, m | 46.81 d | 3.47, m | 46.84 d |
| 12 | | 203.34 s | | 203.27 s |
| 13 | | 83.81 s | | 83.68 s |
| 14 | | 90.93 s | | 90.96 s |
| 16 | | 157.35 s | | 157.33 s |
| 17 | | 107.58 s | | 107.82 s |
| 18 | | 161.48 s | | 161.37 s |
| 19 | 1.26, 3H, s | 27.69 q | 1.32, 3H, s | 26.96 q |
| 20 | 1.59, m 1.76, m | 41.98 t | 1.64, m 1.75, m | 41.71 t |
| 21 | 1.39, m 2.20, dd, 12.8, 4.0 | 25.18 t | 1.34, m 2.28, dd, 12.8, 4.0 | 25.23 t |
| 22 | 2.49, d, 9.2 | 49.01 d | 2.50, d, 9.2 | 49.01 d |
| 23 | | 83.88 s | | 83.95 s |
| 24 | 1.27, 3H, s | 28.86 q | 1.27, 3H, s | 28.83 q |
| 25 | 1.67, 3H, s | 29.87 q | 1.68, 3H, s | 29.92 q |
| 26 | 2.93-2.98, 2H, m | 29.27 t | 2.80-3.00, 2H, m | 29.29 t |
| 27 | 6.08, t, 7.0 | 138.17 d | 6.09, t, 7.0 | 137.54 d |
| 28 | | 127.64 s | | 127.87 s |
| 29 | | 171.33 s | | 170.34 s |
| 30 | 1.71, 3H, s | 20.73 q | 1.73, 3H, s$^d$ | 20.77 q |
| 31 | 3.09, m 3.25, m | 21.61 t | 3.14, m 3.27, m | 21.63 t |
| 32 | 5.02, m | 122.26 d | 5.00, t, 7.0 | 122.22 d |
| 33 | | 131.48 s | | 131.45 s |
| 34 | 1.69, 3H, s | 18.07 q | 1.72, 3H, s$^d$ | 18.16 q |
| 35 | 1.62, 3H, s$^b$ | $^c$25.66 q | 1.64 3H, s$^e$ | $^f$25.72 q |
| 36 | 1.93-2.04, 2H, m | 22.74 t | 1.97-2.18, 2H, m | 22.76 t |
| 37 | 5.02, t, m | 123.85 d | 5.07, t, 7.0 | 123.83 d |
| 38 | | 131.77 s | | 132.08 s |

TABLE 1-continued $^1$H and $^{13}$C NMR data of 1 and 2$^a$.

| No. | 1 $^1$H | 1 $^{13}$C | 2 $^1$H | 2 $^{13}$C |
|---|---|---|---|---|
| 39 | 1.52, 3H, s | 17.62 q | 1.56, 3H, s | 17.62 q |
| 40 | 1.60, 3H, s$^b$ | $^c$25.65 q | 1.62, 3H, s$^e$ | $^f$25.65 q |

$^a$ $^1$H-NMR, 400 MHz; $^{13}$C-NMR, 100 MHz; CDCl$_3$ ($\delta_H$ 7.24, $\delta_C$ 77.23); δ in ppm (J in Hz).
$^{b-d}$Exchangeable signals.

(B) Biological Effects

Both doxorubicin-resistant (K562/R) and -sensitive K562 (K562/S) cell sublines, purchased from Tianjin Instute of Hematopathy, the Chinese Academy of Medical Sciences, China, were cultured in PRMI1640 (Gibco, USA) medium and supplemented with 10 fetal bovine serums at 37° C. in a humidified incubator with 5% CO$_2$. MTT assay was performed using a reported method [12]. Cell lines were seeded into 96-well plates at 6000 viable cells per well. The test chemicals (ADR, DMSO, Th1 and Th2) with different concentrations were loaded in a final volume of 200 μL per well. After 44 hours of incubation, MTT (5 g/L) was added to each well in a volume of 10 μl and incubated for 4 hours. Afterwards, the medium was removed and 200 μl of Me2SO (37° C.) was added and shaken for 5 minutes. A 96-well microtiter plate reader was used to determine absorbance values at 570 nm. Mean value of each concentration (n=3 wells) was obtained. Absorbance of untreated controls was taken as 100%. Survival rate was calculated as follows: Cell survival rate (%)=(T−B)/(U−B)×100%, T (treated) is absorbance of chemically treated cells, U (untreated) is the absorbance of untreated cells, and B (blank) is the absorbance when neither cells nor chemicals was added. Human liver tissue was obtained from au autopsy sample (male, aged 37) from Dalian Medical University, with the approval of the ethics committee of Dalian Medical University. HLM were prepared from liver tissue as described in the literature [13]. Protein concentrations of the microsomal fractions were determined by the Lowry method using bovine serum albumin as a standard. The inhibition effects of compounds were characterized using HLM toward six human cytochrome P-450 enzymes based on their probe reaction. Each incubation was performed in a 100 mM phosphate buffer at pH 7.4 containing human microsomal protein, 10 mM glucose 6-phosphate, 1 mM NADP$^+$, 4 mM magnesium chloride, 1 unit/ml of glucose 6-phosphate dehydrogenase, and various probe substrates of CYPs and tested compounds (previously dissolved in methanol, whose final concentration was 1%, v/v) with a range of concentrations in a total volume of 400 μL. The selective inhibitors of each CYP isoform [Furafylline (1A2), 8-Methoxypsoralen (2A6), Sulphaphenazole (2C9), Quinidine (2D6), Clomethiazole (2E1), Ketoconazole (3A4)] were selected as the positive control. There was a 3 minutes preincubation step at 37° C. before the reaction was started by the addition of NADP$^+$. After 10 min, the reactions were quenched by adding the same volume of CH$_3$CN or MeOH and an internal standard. The incubation mixtures were then centrifuged for 10 minutes at 20,000×g. An aliquot of the supernatant was analyzed by HPLC. The HPLC system (SHIMADZU, Japan) consisted of an SCL-10A system controller, two LC-10AT pumps, a SIL-10A auto injector, a SPD-10AV UV detector or a RF-10A$_{XL}$ fluorescence detector. The supernatant was analyzed using a SHIMADZU C$_{18}$ column (4.6× 150 mm, 5μ) at a flow rate of 1 mL/min. IC$_{50}$ values (concentration of inhibitor causing 50% inhibition of original enzyme activity) were calculated by Microsoft Excel software (Microsoft Inc, USA).

TABLE 2

The in vitro reaction and detection conditions for CYP-isoform bioassay.

| CYPs | Substrate | Reaction | Concentration of Substrate (μM) | Concentration of microsomes (mg/ml) | Time (min) | Internal Standard | Detection of HPLC |
|---|---|---|---|---|---|---|---|
| 1A2 | Phenacetin | O-deethylation | 40 | 0.2 | 30 | 7-Hydroxycoumarin | A (methanol):B(phosphate buffer, pH = 3.0, 50 mM) = 34:66, UV 245 nm |
| 2A6 | Coumarin | 7-hydroxylation | 1 | 0.1 | 10 | — | A (acetonitrile):B water/acetic acid (70:0.1, v/v) = 30:70, Fluo Ex 340 nm, Em 456 nm |
| 2C9 | Diclofenac | 4'-hydroxylation | 10 | 0.3 | 10 | Coumarin | A (acetonitrile):B (phosphate buffer, pH = 7.4, 100 mM) = 32:68, 0-9 min, B 68%-32%, UV 280 nm |
| 2D6 | Dextromethorphan | O-demethylation | 25 | 0.3 | 20 | — | A (acetonitrile):B (phosphate buffer, pH = 3.0, 0.12% Triethylamine) = 25:75, Fluo Ex 235 nm, Em 310 nm |
| 2E1 | Chlorzoxazone | 6-hydroxylation | 120 | 0.4 | 30 | Phenacetin | A (acetonitrile):B (0.5% acetic acid) = 22:60, 0-10 min, B 78%-40% UV 287 nm |
| 3A4 | Testosterone | 6β-hydroxylation | 50 | 0.5 | 10 | Corticosterone | A (methanol):B (water) = 52:48, 0-15 min, B 48-30, 15-20 min 30-20, UV 254 nm |

Example 2

30-Hydroxygambogic Acid and 30-Hydroxyepigambogic Acid (A) Isolation and Identification Plant Materials: The resin of *Garcinia hanburyi* was purchased in Guangzhou, P. R. China. A voucher specimen (CMS-0283) was deposited in the Herbarium of Hong Kong Jockey Club Institute of Chinese Medicine, Hong Kong, China.

Extraction and Isolation: The resin (1 g) was dissolved in 10 mL acetone, and loaded on the preparative HPLC system (Agilent 1100, Alltima $C_{18}$, 10μ, 22×250 mm) to give the mixture (40 mg, $t_R$=8.5 min). The mobile phase was MeOH/0.1% $H_3PO_4$ (90:10). The flow rate was 1 mL/min. UV detection wavelength was set at UV 360 nm. The isolated mixture was further loaded on $C_8$ column (Alltima $C_8$, 5μ, 9.2×250 mm) eluted with $CNCH_3$/0.1% acetic acid/50% 1,4-dioxan (65:25:10) to yield compound 1 (6 mg) and compound 2 (8 mg), which was subsequently identified as 30-hydroxygambogic acid and 30-hydroxyepigambogic acid, respectively.

1D and 2D NMR spectra: Brucker AM-400 and DRX-500 spectrometers; δ in ppm, J in Hz, $Me_4Si$ as internal standard, measured in $C_5D_5N$. MS spectra: VG Autospec-3000 spectrometer; m/z (rel. %). LC/MS analysis was performed using an Agilent 1100 series combined with MICROMASS Q-TOF-2 spectrometer.

30-hydroxygambogic acid (1): A yellow amorphous powder with little sublimability. $[\alpha]_D^{28.0}$=−500.64° (c=0.314, $CHCl_3$). Positive ESI-MS: 645 [M+H]+; positive HRESIMS: 645.3059 ($C_{38}H_{45}O_9$; calc. 645.3063). $^1$H-NMR ($CDCl_3$, 400 MHz) and $^{13}$C-NMR ($CDCl_3$, 100 MHz): see Table 3.

30-hydroxyepigambogic acid (2): A yellowish amorphous powder with a little sublimability. $[\alpha]_D^{28.0}$=−405.57° (c=0.288, $CHCl_3$). Positive ESI-MS: 645 [M+H]+; positive HRESIMS: 645.3054 ($C_{38}H_{45}O_9$; calc. 645.3063). $^1$H-NMR ($CDCl_3$, 400 MHz) and $^{13}$C-NMR ($CDCl_3$, 100 MHz): see Table 3.

TABLE 3

$^1$H-(400 mhz) and/or $^{13}$C-(100 mhz) NMR Data of 30-Hydroxygambogic Acid and 30-Hydroxyepigambogic Acid

|  | 1 | | 2 | |
|---|---|---|---|---|
|  | $\delta_H$ | $\delta_C$ HMBC (position) | $\delta_H$ | $\delta_C$ HMBC (position) |
| C (2) |  | 81.4 3, 4, 19, 20, 36 |  | 81.3 4, 19, 20, 36 |
| CH (3) | 5.36 (d, J = 10.0) | 124.7 4, 19, 20 | 5.44 (d, J = 10.0) | 125.0 4, 19, 20 |
| CH (4) | 6.57 (d, J = 10.0) | 115.7 3 | 6.62 (d, J = 10.0) | 115.8 3 |
| C (5) |  | 102.8 3, 4 |  | 103.0 3, 4 |
| C (6) |  | 157.4 4 |  | 157.5 4 |
| C (7) |  | 100.5 |  | 100.5 |
| C (8) |  | 179.0 10 |  | 179.1 10 |
| C (9) |  | 133.2 10, 11 |  | 133.1 10, 11 |
| CH (10) | 7.53 (d, J = 6.8) | 135.8 11, 21 | 7.56 (d, J = 6.8) | 135.8 11, 21 |
| CH (11) | 3.48 (m) | 46.8 10, 21, 22 | 3.49 (m) | 46.9 10, 21, 22 |

TABLE 3-continued $^1$H-(400 mhz) and/or $^{13}$C-(100 mhz) NMR Data of 30-Hydroxygambogic Acid and 30-Hydroxyepigambogic Acid

|  | 1 | | | 2 | | |
|---|---|---|---|---|---|---|
|  | $\delta_H$ | $\delta_C$ | HMBC (position) | $\delta_H$ | $\delta_C$ | HMBC (position) |
| C (12) |  | 203.2 | 10, 11, 26 |  | 203.1 | 10, 11, 26 |
| C (13) |  | 83.7 | 11, 21, 26, 27 |  | 83.6 | 11, 21, 26, 27 |
| C (14) |  | 90.9 157.3 | 10, 26 |  | 90.9 157.3 | 10, 26 |
| C (16) |  | 157.3 | 31 |  | 157.4 | 31 |
| C (17) |  | 107.7 | 31, 32 |  | 108.0 | 31, 32 |
| C (18) |  | 161.6 | 4, 31 |  | 161.5 | 4, 31 |
| Me—C (19) | 1.36 (s, 3H) | 27.7 | 3, 20 | 1.35 (s, 3H) | 27.6 | 3, 20 |
| CH$_2$ (20) | 1.57, 1.74 (m, each 1H) | 41.9 | 3, 19, 36, 37 | 1.57, 1.74 (m, each 1H) | 41.7 | 3, 19, 36, 37 |
| CH$_2$ (21) | 2.34, 1.40 (m, each 1H) | 25.1 | 10, 11, 22 | 2.34, 1.40 (m, each 1H) | 25.1 | 10, 11, 22 |
| CH (22) | 2.52 (d, J = 9.2) | 48.9 | 11, 21, 24, 25 | 2.53 (d, J = 9.2) | 48.9 | 11, 21, 24, 25 |
| C (23) |  | 84.1 | 21, 22, 24, 25 |  | 84.1 | 21, 24, 25 |
| Me—C (24) | 1.24 (s, 3H) | 28.8 | 22, 25 | 1.29 (s, 3H) | 28.8 | 22, 25 |
| Me—C (25) | 1.67 (s, 3H) | 29.9 | 22, 24 | 1.70 (s, 3H) | 29.9 | 22, 24 |
| CH$_2$ (26) | 3.00 (d, J = 6.8, 2H) | 29.1 | 27 | 2.98 (d, J = 6.8, 2H) | 29.1 | 27 |
| CH (27) | 6.39 (t, J = 7.6) | 140.5 | 26, 30 | 6.39 (t, J = 7.6) | 140.5 | 26, 30 |
| C (28) |  | 131.0 | 26, 27, 30 |  | 131.2 | 26, 27, 30 |
| C (29) |  | 169.9 | 27, 30 |  | 169.9 | 27, 30 |
| CH$_2$ (30) | 4.09, 4.01 (d, J = 13.2) | 64.7 | 27 | 4.13, 4.04 (d, J = 13.2) | 64.7 | 27 |
| CH$_2$ (31) | 3.27, 3.14 (m, each 1H) | 21.6 | 32 | 3.30, 3.16 (m, each 1H) | 21.6 | 32 |
| CH (32) | 5.01 (t, J = 7.6) | 122.0 | 31, 34, 35 | 5.04 (t, J = 7.6) | 122.0 | 31, 34, 35 |
| C (33) |  | 131.8 | 31, 32, 34, 35 |  | 131.7 | 31, 32, 34 35 |
| Me—C (34) | 1.70 (s, 3H) | 18.1 | 32, 25 | 1.74 (s, 3H) | 18.2 | 32, 25 |
| Me—C (35) | 1.61 (s, 3H) | 25.6 | 32, 34 | 1.64 (s, 3H) | 25.7 | 32, 34 |
| CH$_2$ (36) | 2.00 (m, 2H) | 22.7 | 20, 37 | 2.08 (m, 2H) | 22.5 | 20, 37 |
| CH (37) | 5.01 (t, J = 7.6) | 123.7 | 20, 36, 39, 40 | 5.10 (t, J = 7.6) | 123.7 | 20, 36, 39 40 |
| C (38) |  | 131.8 | 36, 37, 39 40 |  | 132.3 | 36, 37, 39 40 |
| Me—C (39) | 1.52 (s, 3H) | 17.6 | 37, 40 | 1.59 (s, 3H) | 17.6 | 37, 40 |
| Me—C (40) | 1.62 (s, 3H) | 25.6 | 37, 39 | 1.67 (s, 3H) | 25.7 | 37, 39 |
| OH—C (6) | 12.74 (s) |  |  | 12.77 (s) |  |  |

(B) Biological Effects

Cytotoxicity Assay: Both epimers were tested for their cytotoxicities against human leukemia K562 (K562/S) and doxorubicin-resistant K562 (K562/R) cell lines, using the SRB method previously described with doxorubicin being the positive control. The OD data were recorded in X±S, and the IC$_{50}$ values were calculated with sigmoidal plot. The result is presented in Table 4.

TABLE 4

Cytotoxicities (IC$_{50}$, μM) of GA derivatives against K562 cell lines

|  | Doxorubicin[a] | Gambogic acid[a] | Epigambogic acid[a] | Doxorubicin | 1 | 2 |
|---|---|---|---|---|---|---|
| K562/R | 10.78 | 1.32 | 1.11 | 1.79 ± 0.17 | 2.89 ± 0.35 | 4.49 ± 0.31 |
| K562/S | 0.66 | 0.89 | 0.86 | 0.11 ± 0.01 | 1.27 ± 0.15 | 3.61 ± 0.17 |

Example 3

Isogambogic Acid and Isoepigambogic Acid

This pair of epimers was isolated in the same way as above described. Specifically, the resin (90 mg) was dissolved in 2 mL acetone, and loaded on the preparative HPLC system (Agilent 1100, Alltima $C_{18}$, 10μ, 22×250 mm) to give GA. The mobile phase was MeOH/0.1% $H_3PO_4$ (90:10). The flow rate was 1 mL/min. UV detection wavelength was set at UV 360 nm. After the isolation with prep-HPLC, the fraction (isogambogic acid and epiisogambogic acid) was condensed to remove most of $CH_3CN$, and the condensed acidified solution was diluted with a large amount of water and loaded on a Sephadex LH-20 CC to remove the acid by eluting with $H_2O$. The subsequent $Me_2CO$ elution was condensed to dry, and the mixture of isogambogic acid and epiisogambogic acid was obtained (35 mg). In the HPLC/ESIMS analysis, the mixture presented as one peak (m/z 628) on $C_{18}$ column (Alltima $C_{18}$, 5μ, 4.6×250 mm) eluted with $CH_3CN$/0.1% acetic acid (90:10). However, two completely separated peaks appeared with $C_8$ column (Alltima $C_8$, 5μ, 4.6×250 mm) eluted with $CH_3CN$/0.1% acetic acid (75:25). These two peaks, which were subsequently identified as isogambogic acid and epiisogambogic acid, respectively, were isolated by HPLC under the same analytical condition with each injection of 20 μL acetone solution of the mixture.

Isogambogic acid (1) obtained was a bright yellow amorphous powder. $[\alpha]_D^{20}=-660°$ (c=0.321, $CHCl_3$). ESIMS: m/z=629 ($[M+H]^+$); (+)FABMS: m/z=629 ($[M+H]^+$); HRESIMS: m/z=obsd. 629.3133 $[M+H]^+$, calcd. 629.3114. Epiisogambogic acid (2) was also a bright yellow amorphous powder. $[\alpha]_D^{20}=-587°$ (c=0.261, $CHCl_3$). ESIMS: m/z=629 ($[M+H]^+$); (+)FABMS: m/z=629 ($[M+H]^+$); HRESIMS: m/z=obsd. 629.3101 $[M+H]^+$, calcd. 629.3114. More analytic data are shown in the following table 5:

TABLE 3

$^1$H- (400 mhz) and/Or $^{13}$C- (100 mhz) NMR Data of Isogambogic Acid and Epiisogambogic Acid

| No. | Isogambogic acid $^1$H | Isogambogic acid $^{13}$C | Epiisogambogic acid $^1$H | Epiisogambogic acid $^{13}$C |
|---|---|---|---|---|
| 2 | | 81.43 s | | 81.27 s |
| 3 | 5.43, d, 10.0 | 124.87 d | 5.44, d, 10.0 | 124.79 d |
| 4 | 6.65, d, 10.0 | 116.03 d | 6.66, d, 10.0 | 115.97 d |
| 5 | | 102.89 s | | 102.91 s |
| 6 | | 157.71 s | | 157.60 s |
| 6-OH | 12.75 s | | 12.74 s | |
| 7 | | 100.47 s | | 100.46 s |
| 8 | | 178.90 s | | 178.85 s |
| 9 | | 133.44 s | | 133.39 s |
| 10 | 7.54, d, 7.2 | 135.40 d | 7.53, d, 6.8 | 135.50 d |
| 11 | 3.49, m | 46.95 d | 3.49, m | 46.94 d |
| 12 | | 203.13 s | | 202.99 s |
| 13 | | $^b$83.74 s | | $^e$83.61 s |
| 14 | | 90.80 s | | 90.60 s |
| 16 | | 157.43 s | | 157.34 s |
| 17 | | 108.00 s | | 107.88 s |
| 18 | | 161.52 s | | 161.29 s |
| 19 | 1.38, 3H, s | 27.61 q | 1.37, 3H, s | 27.34 q |
| 20 | 1.61, m 1.78, m | 41.98 t | 1.60, m 1.80, m | 41.87 t |
| 21 | 1.40, m 2.31, dd, 12.8, 4.0 | 25.18 t | 1.34, m 2.32, dd, 12.8, 4.0 | 25.47 t |
| 22 | 2.52, d, 9.2 | 49.01 d | 2.52, d, 9.2 | 49.02 d |
| 23 | | $^b$83.85 s | | $^e$83.67 s |
| 24 | 1.28, 3H, s | 29.03 q | 1.27, 3H, s | 29.05 q |
| 25 | 1.70, 3H, s | 30.02 q | 1.70, 3H, s | 30.02 q |
| 26 | 2.64, m 2.55, m | 29.03 t | 2.60-2.62, 2H, m | 29.05 t |
| 27 | 6.63, t, 7.2 | 137.15 d | 6.51, t, 7.0 | 136.79 d |
| 28 | | 128.62 s | | 128.86 s |
| 29 | | 171.82 s | | 171.47 s |
| 30 | 1.34, 3H, s | 11.48 q | 1.35, 3H, s | 11.39 q |
| 31 | 3.23-3.26, 2H, m | 21.71 t | 3.26-3.28, 2H, m | 21.64 t |
| 32 | 5.09, t, 7.0 | 122.24 d | 5.12, t, 7.0 | 122.10 d |
| 33 | | $^c$131.87 s | | $^f$131.76 s |
| 34 | 1.71, 3H, s | 18.19 q | 1.73, 3H, s | 18.17 q |
| 35 | 1.63, 3H, s | $^d$25.74 q | 1.64, 3H, s | $^g$25.74 q |
| 36 | 2.00-2.05, 2H, m | 22.86 t | 2.03-2.09, 2H, m | 22.75 t |
| 37 | 5.04, t, 7.0 | 123.91 d | 5.06, t, 7.0 | 123.75 d |
| 38 | | $^c$131.93 s | | $^f$131.96 s |
| 39 | 1.53, 3H, s | 17.71 q | 1.55, 3H, s | 17.63 q |
| 40 | 1.63, 3H, s | $^d$25.66 q | 1.64, 3H, s | $^g$25.66 q |

$^a$ $^1$H-NmR, 400 MHz; $^{13}$C-NMR, 100 MHz; $CDCl_3$($\delta_H$ 7.24, $\delta_C$ 77.23); δ in ppm (J in Hz).
$^{b-g}$Exchangeable signals.

Manufacturing Pharmaceutical Compositions Containing Individual Epimers:

As shown in the foregoing, three pairs of epimers were isolated from the herb were separated from the herb gambogges, and were separated from each other. The biological assays showed that each epimer may have useful effects in treating diseases. It is contemplated, as people with ordinary skill in the art would do, that the newly separated compounds may be each individually or in combination used as an ingredient to prepare a pharmaceutical composition for a particular treatment purpose. As it is the status of the art in the pharmaceutical industry, once substantially pure preparations of a compound are obtained, various pharmaceutical compositions or formulations can be prepared from the substantially pure compound using conventional processes or future developed processes in the industry. Specific processes of making pharmaceutical formulations and dosage forms (including, but not limited to, tablet, capsule, injection, syrup) from chemical compounds are not part of the invention and people of ordinary skill in the art of the pharmaceutical industry are capable of applying one or more processes established in the industry to the practice of the present invention. Alternatively, people of ordinary skill in the art may modify the existing conventional processes to better suit the compounds of the present invention. For example, the patent or patent application databases provided at USPTO official website contain rich resources concerning making pharmaceutical formulations and products from effective chemical compounds.

Another useful source of information is Handbook of Pharmaceutical Manufacturing Formulations, edited by Sarfaraz K. Niazi and sold by Culinary & Hospitality Industry Publications Services.

It is further contemplated that the novel compounds of the present invention may be modified in various ways which are known in the art. Therefore the compounds of the present invention encompass all the compounds which are obvious derivatives of the specific compounds disclosed herewith.

The term "pharmaceutical carrier" means an ingredient contained in a drug formulation that is not a medicinally active constituent. The term "an effective amount" refers to the amount that is sufficient to elicit a therapeutic effect on the treated subject. Effective doses will vary, as recognized by those skilled in the art, depending on the types of diseases treated, route of administration, excipient usage, and the possibility of co-usage with other therapeutic treatment. A person skilled in the art may determine an effective amount under a particular situation.

A "pharmaceutically acceptable carrier" is determined in part by the particular composition being administered and in part by the particular method used to administer the composition. A wide variety of conventional carrier may be suitable for pharmaceutical compositions of the present invention and can be selected by people with ordinary skill in the art.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

REFERENCES

1 L. J. Lin, L. Z. Lin, J. M. Pezzuto, G. A. Cordell, *Magn. Reson. Chem.* 1993, 31, 340.

2 J. Asano, K. Chiba, M. Tada, T. Yoshi, *Phytochemistry* 1996, 41, 815.

3 Q. M. Lei, J. M. Liu, *Chin. J. Canc. Prev. & Treat.* 2003, 10, 216.

4 Q. L. Guo, L. Zhao, Q. D. You, Z. Q. Wu, H. Y. Gu. *Chin. J. Nat. Med.* 2004, 2, 106.

5 Q. L. Guo, Q. D. You, S. T. Yuan, L. Zhao, *Acta Pharmacol. Sin.* 2004, 25, 769.

6 L. Zhao, Q. L. Guo, Q. D. You, Z. Q. Wu, H. Y. Gu, *Biol. Pharm. Bull.* 2004, 27, 998.

7 Z. Q. Wu, Q. L. Guo, Q. D. You, L. Zhao, H. Y. Gu, *Biol. Pharm. Bull.* 2004, 27, 1769.

8 T. J. R. Weakley, S. X. Cai, H. Z. Zhang, J. F. W. Keanal, *J. Chem. Crystallogr.* 2001, 31, 501.

9 H. Z. Zhang, S. Kasibhatia, Y. Wang, J. Herich, J. Guastella, B. Tseng, J. Drewe, S. X. Cai. *Bioorg. & Med. Chem.* 2004, 12, 309.

10 Beringer P M, Slaughter R L. Transporters and their impact on drug disposition. Ann Pharmacother 2005; 39: 1097-108

11 Antoniou T, Tseng A L. Interactions between antiretrovirals and antineoplastic drug therapy. Clin Pharmacokinet 2005; 44: 111-45

12 Mosmann T. Rapid calorimetric assay for cellular growth and survival: application to proliferation and cytotoxicity assay. J Immunol method 1983; 65: 5-63

13 Sanderink G J, Bournique B, Stevens J, Petry M, Martinet M. Involvement of human CYP1A isoenzymes in the metabolism and drug interactions of riluzole in vitro. J Pharm Exper Therap 1997; 282: 1465-72

What is claimed is:

1. A compound, which is 30-hydroxygambogic acid.
2. A compound, which is 30-hydroxyepigambogic acid.
3. A pharmaceutical composition, which comprises a pharmaceutically acceptable carrier and an effective amount of a compound of claim 1.
4. A pharmaceutical composition, which comprises a pharmaceutically acceptable carrier and an effective amount of a compound of claim 2.

* * * * *